United States Patent [19]

Niemers et al.

[11] 4,344,939
[45] * Aug. 17, 1982

[54] PENICILLIN 1,1-DIOXIDES, COMPOSITIONS THEREOF AND METHODS OF USE

[75] Inventors: Ekkehard Niemers; Hans-Bodo König; Wilfried Schröck; Karl G. Metzger, all of Wuppertal, Fed. Rep. of Germany

[73] Assignee: Bayer Aktiengesellschaft, Leverkusen, Fed. Rep. of Germany

[*] Notice: The portion of the term of this patent subsequent to Aug. 17, 1999, has been disclaimed.

[21] Appl. No.: 154,541

[22] Filed: May 29, 1980

[30] Foreign Application Priority Data

Jun. 8, 1979 [DE] Fed. Rep. of Germany ....... 2923339

[51] Int. Cl.³ .................. A61K 31/425; A61K 31/43; A61K 31/44; A61K 31/445; A61K 31/505; A61K 31/535; A61K 31/655; C07D 499/52; C07D 499/54; C07D 499/60; C07D 499/76

[52] U.S. Cl. ............................. 424/226; 260/239.1; 424/248.5; 424/251; 424/263; 424/267; 424/270; 424/271; 424/250; 424/269

[58] Field of Search .............. 260/239.1; 424/270, 424/271, 226, 251, 248.51, 263, 267, 269, 250, 248.53

[56] References Cited

U.S. PATENT DOCUMENTS 3,197,466 7/1965 Chow et al. ............. 260/239.1
3,536,698 10/1970 Chauvette et al. ........ 260/239.1

OTHER PUBLICATIONS

Tetrahedron Letters, No. 9, pp. 381-385, (1962).
J. Org. Chem., 28, pp. 1927–1928, (1963).
J. Org. Chem., 38, pp. 940–943, (1973).
J. Chem. Soc. Perkin I, pp. 1772–1775, (1976).

*Primary Examiner*—Natalie Trousof
*Assistant Examiner*—Vera C. Clarke
*Attorney, Agent, or Firm*—Sprung, Horn, Kramer & Woods

[57] ABSTRACT

New penicillin 1,1-dioxides of the formula

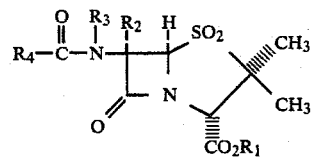

or a salt thereof, in which
$R_1$ denotes a hydrogen atom or an ester-forming radical,
$R_2$ denotes a hydrogen atom,
$R_3$ denotes a hydrogen atom,
$R_4$ denotes a hydrogen atom, an optionally substituted naphthyl radical or a radical of the general formula

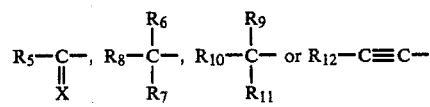

and the remaining variables can be various organic radicals.

8 Claims, No Drawings

PENICILLIN 1,1-DIOXIDES, COMPOSITIONS THEREOF AND METHODS OF USE

The present invention relates to certain new penicillin 1,1-dioxide compounds, to processes for their production, and to their use as medicaments in human medicine and veterinary medicine and as feed additives, and in particular their use as β-lactamase inhibitors.

1,1-Dioxides of various penicillins are described in J. Org. Chem. 28, 1927–1928, J. Org. Chem. 38, 940–943, J. Chem. Soc. 1976, 1772–1775, Tetrahedron Letters No. 9 (1962), 381 and in U.S. Pat. Nos. 3,197,466 and 3,536,698.

According to the present invention we provide compounds which are penicillin 1,1-dioxides of the general formula

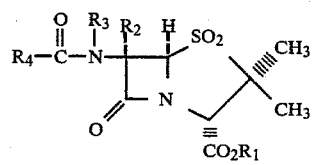

or a salt thereof, in which $R_1$ denotes a hydrogen atom or an ester-forming radical, $R_2$ denotes a hydrogen atom, $R_3$ denotes a hydrogen atom, $R_4$ denotes a hydrogen atom, an optionally substituted naphthyl radical or a radical of the general formula

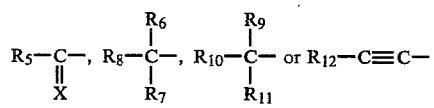

$R_5$ denotes a hydrogen atom, an optionally substituted alkyl radical, an optionally substituted alkoxy radical, an aryloxy or aryl radical, an optionally substituted cycloalkyl radical, an optionally substituted cycloalkenyl radical, an optionally substituted cycloalkadienyl radical, an optionally substituted alkenyl radical, or an optionally substituted aralkyl radical or a heterocyclyl radical, $R_6$ denotes a halogen atom, an optionally substituted alkyl radical, an optionally substituted alkoxy radical, an optionally substituted cycloalkyl radical, an optionally substituted cycloalkenyl radical, an optionally substituted cycloalkadienyl radical, an optionally substituted alkenyl radical, an optionally substituted aralkyl radical, a heterocyclyl radical, an optionally substituted aralkoxy radical, an optionally substituted naphthyl radical, a sulpho group or a functional derivative of the sulpho group, a carboxyl group or a functional derivative of the carboxyl group, a hydroxyl group, an acyloxy radical, an optionally substituted amino group or an optionally substituted cycloalkoxy radical, $R_7$ and $R_8$ independently denote a hydrogen atom, an optionally substituted alkyl radical or an optionally substituted alkoxy radical, with the proviso that $R_7$ and $R_8$ are not alkoxy if $R_6$ is hydroxyl or optionally substituted amino, $R_9$ denotes an optionally substituted phenyl radical, $R_{10}$ denotes an optionally substituted phenyl radical, an optionally substituted alkoxy radical, an optionally substituted alkyl radical, an optionally substituted aralkyl radical, an acyloxy radical, a carboxyl group or a functional derivative of the carboxyl group, a sulpho group, a functional derivative of the sulpho group, an acyl radical, an optionally substituted cycloalkyl radical, an optionally substituted cycloalkenyl radical, an optionally substituted cycloalkadienyl radical, an optionally substituted alkenyl radical, a heterocyclyl radical or a halogen atom and $R_{11}$ independently of $R_{10}$ has any of those meanings given for $R_{10}$ or denotes a hydrogen atom or an optionally substituted amino group, or $R_7$ and $R_8$, or $R_{10}$ and $R_{11}$, together with the carbon atom to which they are bonded, form a carbocyclic or heterocyclic 3-membered to 7-membered ring, $R_{12}$ denotes a hydrogen atom or an optionally substituted alkyl or aryl radical and X denotes an oxygen atom, $R_{13}$—N or

in which $R_{13}$ denotes a hydroxyl group, an optionally substituted alkoxy radical or an optionally substituted amino group or a heterocyclyl radical and $R_{14}$ and $R_{15}$ denote a hydrogen atom, an optionally substituted alkyl radical, an aryl or heterocyclyl radical, a carboxyl group or a functional derivative of the carboxyl group.

Examples of ester-forming radicals $R_1$ are optionally substituted alkyl and optionally substituted aralkyl, aryl and heterocyclyl.

In the general formula (I), optionally substituted alkyl of $R_5$, $R_6$, $R_7$, $R_8$, $R_{10}$, $R_{11}$ and $R_{12}$ is straight-chain or branched alkyl with preferably 1 to 6, especially 1 to 4, carbon atoms. Examples which may be mentioned are optionally substituted methyl, ethyl, n- and i-propyl and n-, i- and t-butyl.

Optionally substituted alkyl of $R_1$ is, for example, $C_1$ to $C_6$ alkyl, preferably $C_1$ to $C_3$-alkyl, which can be mono-, di- or tri-substituted, preferably monosubstituted, by the following substituents: halogen (preferably fluorine, chlorine, bromine or iodine, and especially fluorine, chlorine or bromine); amino; mono-lower alkylamino (preferably ethylamino or, especially methylamino); di-lower alkylamino (preferably diethylamino or, especially, dimethylamino); pyrrolidyl; piperidyl; HCO—NH—; lower alkyl—CO—NH— (preferably $CH_3$—CO—NH—); H—CO—N—(loweralkyl)— (preferably H—CO—N($CH_3$)— or H—CO—N($C_2H_5$)—); lower alkyl-CO-N(lower alkyl)— (preferably $CH_3$-CO-N($CH_3$)); (lower alkyl)$_2$C=N—; lower alkyl—$SO_2$—NH— (preferably $C_2H_5$—$SO_2$—NH— or especially, $CH_3$—$SO_2$—NH—); lower alkyl—$SO_2$—N(lower alkyl)— (preferably $CH_3$—$SO_2$—N($CH_3$)—); HO—$SO_2$—NH—; HO—$SO_2$—N(-lower alkyl)— (preferably HO—$SO_2$—N—($CH_3$)— or HO—$SO_2$—N($C_2H_5$)—); amidino; (lower alkyl)$_2$—N—CH=N— (especially ($CH_3$)$_2$N—CH=N—);

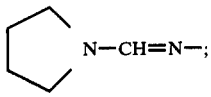

guanido; nitro; azido; hydroxyl; lower alkoxy (preferably $C_2H_5$—O— or, especially $CH_3O$—); H—CO—O—; lower alkyl—CO—O— (preferably $CH_3$—CO—O, $C_2H_5$—CO—O— or $(CH_3)_3C$—CO—O—); lower alkyl—O—CO—O—, (preferably $CH_3$—O—CO—O—, $C_2H_5$—O—CO—O— or $(CH_3)_3C$—O—CO—O—); $H_2N$—CO—O—; lower alkyl—NH—CO—O— (preferably $CH_3$—NH—CO—O or $C_2H_5$—NH—CO—O—); (lower alkyl)$_2$N—CO—O— (preferably $(CH_3)_2N$—CO—O— or $(C_2H_5)_2N$—CO—O—);

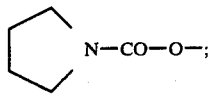

$H_2N$—$SO_2$—O—; lower alkyl—NH—$SO_2$—O— (preferably $CH_3$—NH—$SO_2$—O— or $C_2H_5$—NH—$SO_2$—O—); (lower alkyl)$_2$N—$SO_2$—O—, (preferably $(CH_3)_2N$—$SO_2$—O— or $(C_2H_5)_2N$—$SO_2$—O—); HOOC—; $H_2N$—CO—; (lower alkyl)$_2$N—CO— (especially $(CH_3)_2N$—CO— or $(C_2H_5)_2N$—CO—); OHC—; HO—$SO_2$—O—; HS—; lower alkyl—S—, (preferably $CH_3$—S—, $CF_3$—S—, $C_2H_5$—S— or $(CH_3)_2CH$—S—);

lower alkyl—$SO_2$— (preferably $CH_3$—$SO_2$—, $CF_3SO_2$— or $C_2H_5$—$SO_2$—); $H_2N$—$SO_2$—; lower alkyl—NH—$SO_2$— (preferably $CH_3$—NH—$SO_2$— or $C_2H_5$—NH—$SO_2$—); (lower alkyl)$_2$N—$SO_2$— (preferably $(CH_3)_2N$—$SO_2$— or $(C_2H_5)_2N$—$SO_2$—);

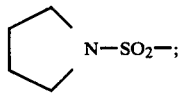

HO—$SO_2$—S—; heterocyclyl, preferably furyl, thienyl, pyridyl or 2-oxo-benzimidazolinyl); lower alkylcarbonyl (especially acetyl); benzoyl; lower dialkylamino-lower alkoxycarbonyloxy (especially dimethylamino- or diethylamino-$C_1$-$C_2$-alkoxycarbonyloxy); morpholino-, piperidino- or pyrrolidino-$C_1$-$C_2$-alkoxycarbonyloxy; lower alkoxycarbonylamino; or lower alkylcarbonylthio.

Optionally substituted alkenyl of $R_5$, $R_6$, $R_{10}$ and $R_{11}$ is straight-chain or branched alkenyl with preferably 2 to 6, especially 2 to 4, carbon atoms. Examples which may be mentioned are optionally substituted vinyl, propen-1-yl, propen-2-yl, buten-3-yl and buten-2-yl.

Optionally substituted cycloalkyl, cycloalkenyl and cycloalkadienyl of $R_5$, $R_6$, $R_{10}$ and $R_{11}$ is monocyclic, bicyclic or tricyclic and preferably contains 3 to 10, especially 3, 5 or 6 carbon atoms. Examples which may be mentioned are optionally substituted cyclopropyl, cyclobutyl, cyclopentyl, cyclopentenyl, cyclohexyl, cyclohexenyl, cyclohexadienyl, cycloheptyl, bicyclo[2.2.1]-heptyl, bicyclo-[2.2.2]-octyl and adamantyl.

Optionally substituted aryl of $R_1$, $R_5$ and $R_{12}$ and aryloxy of $R_5$ is aryl, or aryloxy, with preferably 6 to 10 carbon atoms in the aryl part. Examples which may be mentioned are optionally substituted phenyl or naphthyl. Substituents in the phenyl ring are in the o-, m- or p-position.

Optionally substituted aralkyl of $R_1$, $R_5$, $R_6$, $R_{10}$ and $R_{11}$ and aralkoxy of $R_6$ is aralkyl or aralkoxy which is optionally substituted in the aryl part and/or alkyl part and has preferably 6 or 10, especially 6, carbon atoms in the aryl part and preferably 1 to 4, especially 1 or 2, carbon atoms in the alkyl part, it being possible for the alkyl part to be straight-chain or branched. Examples which may be mentioned are optionally substituted benzyl and phenylethyl.

Optionally substituted heterocyclyl of $R_1$, $R_5$, $R_6$, $R_{10}$, $R_{11}$, $R_{13}$, $R_{14}$ and $R_{15}$ is a hetero-paraffinic, hetero-aromatic or hetero-olefinic 5-membered to 7-membered, preferably 5-membered or 6-membered, ring with preferably 1 to 3, especially 1 or 2, identical or different hetero-atoms. Hetero-atoms are oxygen, sulphur or nitrogen. Examples which may be mentioned are optionally substituted thienyl, furyl, oxazolyl, isoxazolyl, thiazolyl, isothiazolyl, pyrrolyl, imidazolyl, pyrazolyl, oxadiazolyl, thiadiazolyl, triazolyl, oxtriazolyl, thiatriazolyl, tetrazolyl, pyridyl, pyrazinyl, pyrimidinyl, tetrahydrofuranyl, dioxanyl, pyrrolidinyl, piperidinyl, morpholinyl, pyron-2-yl and pyron-4-yl, 2-oxo-tetrahydrofur-5-yl and 2-oxo-2,5-dihydrofur-5-yl.

The abovementioned alkyl, alkenyl, cycloalkyl, cycloalkenyl, cycloalkadienyl, aryl and aralkyl, and optionally substituted naphthyl of $R_4$ and optionally substituted phenyl of $R_9$, $R_{10}$ and $R_{11}$ can carry one or more, preferably 1 to 3, especially 1 or 2, identical or different radicals preferably those defined as $R_{16}$ below.

Very particularly preferred radicals are the radicals mentioned which are unsubstituted or contain one substituent $R_{16}$.

Heterocyclyl can contain one or more, preferably 1 to 3, especially 1 or 2, identical or different radicals, preferably those defined as $R_{17}$ below. A very particularly preferred radical is heterocyclyl which is unsubstituted or contains one substituent $R_{17}$.

In the following explanations, the expression "lower alkyl" in all cases, also in connection with other atoms or groups (for example lower alkoxy, NCON(lower alkyl))denotes straight-chain or branched alkyl with preferably 1 to 6, especially 1 to 4, carbon atoms. Examples which may be mentioned are optionally substituted methyl, ethyl, n- and i-propyl and n-, i- and t-butyl. "Lower alkyl" can be substituted by 1 to 5, especially 1 to 3, identical or different halogen atoms (halogen atoms being preferably, fluorine, chlorine and bromine, especially fluorine and chlorine). Trifluoromethyl, chloro-difluoromethyl, bromomethyl, 2,2,2-trifluoroethyl and pentafluoroethyl may be mentioned as examples.

$R_{16}$ denotes halogen (preferably fluorine, chlorine, bromine or iodine, and especially fluorine, chlorine or bromine); amino; mono-lower alkylamino (preferably ethylamino or, especially, methylamino); di-lower alkylamino (preferably diethylamino or, especially, dimethylamino); pyrrolidyl; piperidyl; HCO—NH—; lower alkyl—CO—NH— (preferably $CH_3$—CO—NH—); H—CO—N(lower alkyl)— (preferably H—CO—N($CH_3$)— or H—CO—N($C_2H_5$—); di-lower alkylamino-lower alkyl; lower alkyl—CO—N(lower alkyl)— (preferably CH₃—CO—N(CH₃)—); (lower alkyl)₂C=N—; lower alkyl—SO₂—NH—, (preferably C₂H₅—SO₂—NH— or, especially CH₃—SO₂—NH—); lower alkyl—SO₂—N(lower alkyl)— (preferably CH₃—SO₂—N(CH₃)—); HO—SO₂—NH—; HO—SO₂—N(lower alkyl)— (preferably HO—SO₂—N—(CH₃)— or HO—SO₂—N(C₂H₅)—); amidino; (lower alkyl)₂—N—CH=N— (especially (CH₃)₂N—CH=N—);

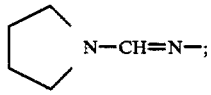

guanido; nitro; azido; hydroxyl; lower alkoxy (preferably C₂H₅—O— or, especially, CH₃O—); H—CO—O—; lower alkyl—CO—O— (preferably CH₃—CO—O, C₂H₅—CO—O— or (CH₃)₃C—CO—O—); lower alkyl—O—CO—O— (preferably CH₃—O—CO—O—, C₂H₅—O—CO—O— or (CH₃)₃C—O—CO—O—); H₂N—CO—O—; lower alkyl—NH—CO—O— (preferably CH₃—NH—CO—O— or C₂H₅—NH—CO—O—); (lower alkyl)₂N—CO—O— (preferably (CH₃)₂N—CO—O— or (C₂H₅)₂N—CO—O—);

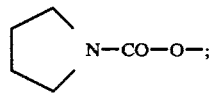

H₂N—SO₂—O—; lower alkyl—NH—SO₂—O— (preferably CH₃—NH—SO₂—O— or C₂H₅—NH—SO₂—O—); (lower alkyl)₂N—SO₂—O—, (preferably (CH₃)₂N—SO₂—O— or (C₂H₅)₂N—SO₂—O—); HOOC—; H₂N—CO—; (lower alkyl)₂N—CO— (especially (CH₃)₂N—CO— or (C₂H₅)₂N—CO—); OHC—; HO—SO₂—O—; HS—; lower alkyl—S—, (preferably CH₃—S—, CF₃—S—, C₂H₅—S— or (CH₃)₂CH—S—);

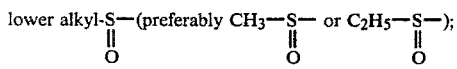

HO₃S—; lower alkyl—SO₂— (preferably CH₃—SO₂—, CF₃SO₂— or C₂H₅—SO₂—); H₂N—SO₂—; lower alkyl—NH—SO₂—, (preferably CH₃—NH—SO₂— or C₂H₅—NH—SO₂—); (lower alkyl)₂N—SO₂— (preferably (CH₃)₂N—SO₂— or (C₂H₅)₂N—SO₂—);

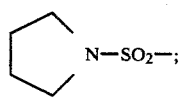

HO—SO₂—S—; straight-chain or branched alkyl with 1 to 6 carbon atoms (preferably ethyl, propyl, isopropyl, n-butyl, sec-butyl or tert.-butyl or, especially, methyl); and phenyl or phenoxy.

In the case where R₁₇ is on one or more carbon atoms in the heterocyclyl radical, R₁₇ preferably denotes lower alkyl (preferably ethyl or isopropyl or, especially, methyl); the trifluoromethyl group; halogen, (preferably fluorine, chlorine or bromine); amino; lower alkyl-amino (preferably CH₃—NH— or C₂H₅—NH—); di-lower alkylamino (preferably (CH₃)₂N— or (C₂H₅)₂N—); formylamino; acetylamino; CH₃—O—CO—NH— or C₂H₅O—CO—NH—; CH₃—SO₂—NH—; hydroxyl; methoxy or ethoxy; methylthio or ethylthio; CH₃—SO₂—; CH₃—SO—; HOOC—; HO₃S—; HCO—; lower alkyl—CO— (preferably CH₃—CO—); lower alkyl—O—CO— (preferably CH₃—O—CO— or C₂H₅O—CO—); or —CN.

In the case where R₁₇ in a nitrogen-containing heterocyclyl radical is a substituent on one or more nitrogen atoms, R₁₇ preferably denotes lower alkyl (preferably propyl or isopropyl or, especially, methyl or ethyl); the group —C=N; —CHO; —COO—lower alkyl (preferably —COO—CH₃, —COOC₂H₅, —COOCH(CH₃)₃); —CO—NH₂; —CO—NH—lower alkyl (preferably —CO—NH—CH₃, —CO—NH—C₂H₅ or —CO—NH—CH(CH₃)₂); or —CO—lower alkyl (preferably —CO—CH₃, —CO—C₂H₅ or —CO—CH(CH₃)₂).

The rings which can be formed from R₇ and R₈, or R₁₀ and R₁₁, together with the carbon atom to which they are bonded, are saturated or unsaturated. Unsaturated rings preferably contain 1 or 2 double bonds. The rings can contain 1 or more, preferably 1 or 2, and especially 1, hetero-atoms or hetero-groups. Heteroatoms which may be mentioned are oxygen, sulphur and/or nitrogen. Examples of hetero-groups which may be mentioned are the SO₂ group and the lower alkyl-N-group, and in the case of 6-membered rings, a hetero-atom or a hetero-group is preferably in the 4-position (relative to the carbon atom bearing the free bond). Particularly preferred rings which may be mentioned are:

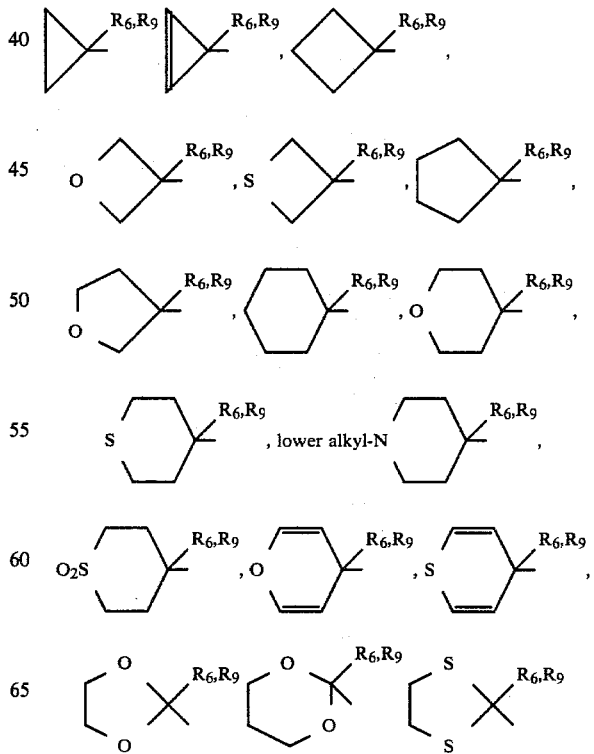

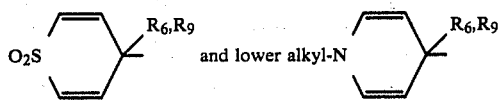

The rings which are formed by $R_7$ and $R_8$, or $R_{10}$ and $R_{11}$, together with the carbon atom to which they are bonded, can contain one or more, preferably 1 to 3 and especially 1 or 2, identical or different substituents, especially halogen (preferably fluorine, chlorine and bromine); hydroxyl; lower alkoxy (preferably methoxy and ethoxy); lower alkylthio (preferably methylthio and ethylthio); amino; lower alkylamino, (preferably $CH_3-NH-$ and $C_2H_5-NH-$); di-lower alkylamino, (preferably dimethylamino and diethylamino); —CN; —COOH; —COOCH$_3$; —COOC$_2$H$_5$; and straight-chain or branched lower alkyl (preferably methyl and ethyl).

Optionally substituted alkoxy of $R_5$, $R_6$, $R_7$, $R_8$, $R_{10}$, $R_{11}$ and $R_{13}$ is, for example, alkoxy which has 1 to 6, especially 1 to 3, carbon atoms and can be monosubstituted or polysubstituted, preferably monosubstituted, preferably by $R_{16}$ as defined above.

Functional derivatives of the carboxyl groups of $R_6$, $R_{10}$, $R_{14}$ and $R_{15}$ are ester groups as defined above for $R_1$, carboxylic acid amide groups, it being possible for the nitrogen atom to be substituted in a manner corresponding to the optionally substituted amino groups of $R_{11}$ and $R_{13}$, cyano and corresponding thio analogues. Functional derivatives of the sulpho groups are, in particular, sulphonamide groups, it being possible for the nitrogen to be substituted in a manner corresponding to the optionally substituted amino groups of $R_{11}$ and $R_{13}$.

Acyl of $R_{10}$ and $R_{11}$ and acyl in acyloxy of $R_6$, $R_{10}$ and $R_{11}$ are, especially, optionally substituted alkylcarbonyl, arylcarbonyl, aralkylcarbonyl, optionally substituted alkenylcarbonyl, optionally substituted cycloalkylcarbonyl, optionally substituted cycloalkenylcarbonyl or optionally substituted cycloalkadienylcarbonyl, or the corresponding sulphonyl radicals, and furthermore optionally substituted alkoxycarbonyl or optionally substituted aminocarbonyl, alkyl, alkenyl, aralkyl, aryl, cycloalkyl, cycloalkenyl, cycloalkadienyl, alkoxy and amino corresponding to the abovemention definitions.

Optionally substituted amino is NH$_2$ or mono- or di-substituted amino, possible substituents being optionally substituted alkyl, optionally substituted alkenyl, aryl, optionally substituted aralkyl, heterocyclyl, optionally substituted cycloalkyl, optionally substituted cycloalkenyl and optionally substituted cycloalkadienyl, the meanings of the amino substituents corresponding to the abovementioned definitions of the individual radicals.

Preferred compounds of the present invention are those of the general formula

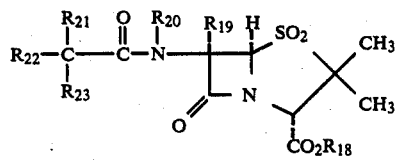

in which $R_{18}$ denotes a hydrogen atom, a sodium ion,

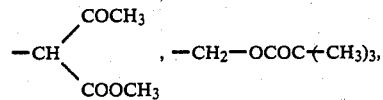

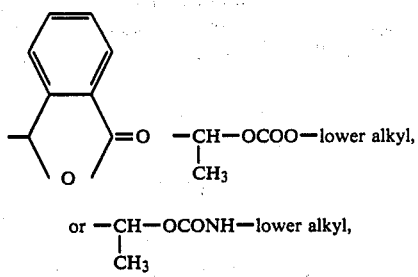

$R_{19}$ denotes a hydrogen atom,
$R_{20}$ denotes a hydrogen atom,
$R_{21}$ and $R_{22}$ independently of each other denote an optionally substituted $C_1$ to $C_4$ alkyl radical, an optionally substituted $C_1$ to $C_4$ alkoxy radical or, both together with the carbon atom to which they are bonded, denote a dioxacyclopentane or dioxacyclohexane ring and
$R_{23}$ denotes an optionally substituted $C_1$ to $C_4$ alkyl radical, an optionally substituted $C_1$ to $C_4$ alkoxy radical or a phenyl, furyl, thienyl, methylisoxazolyl or aminothiazolyl radical.

Surprisingly, the compounds according to the invention exhibit a considerably more powerful inhibiting action on β-lactamases than the penicillin 1,1-dioxides known from the state of the art. The compounds according to the invention thus represent an enrichment of the range of medicaments.

According to the present invention we further provide a process for the production of compounds of the invention in which, (a) a compound of the general formula

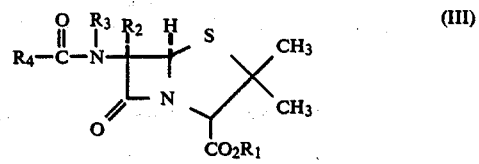

in which $R_1$, $R_2$, $R_3$ and $R_4$ have the meaning indicated above, is oxidized in a solvent, or (b) a 6-aminopenicillanic acid 1,1-dioxide of the general formula

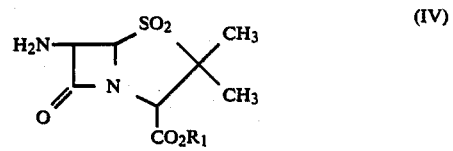

or a salt or an ester thereof or a derivative thereof reactivated on the amino group, in which $R_1$ has the meaning indicated above, is reacted with a compound of the formula

or a reactive carboxylic acid derivative or a salt thereof, R₄ having the abovementioned meaning.

The substituted penicillins of the formula (III) used as starting compounds in reaction variant (a) are either already known, or they can be prepared by known processes, for example by acylation of 6-aminopenicillianic acid or esters thereof.

Possible solvents for reaction variant (a) are, in particular, polar solvents, for example water, acetic acid and tetrahydrofuran, and mixtures of these three. The reaction temperatures are in general between −20° and +50° C., preferably between 0° and 20° C. The reaction is in general carried out under normal pressure. The pH value of the reaction solution is in general between 2 and 8, preferably between 3.5 and 7.5.

In each case stoichiometric amounts of the reactants are preferably employed in carrying out the reaction variant (a). However, it is in all cases possible to add one of the reactants in excess, preferably the oxidizing agent. The reaction products are worked up by the methods customary in preparative organic chemistry.

The oxidation is preferably carried out with the following oxidizing agents: potassium permanganate, ozone, hydrogen peroxide, hydrogen peroxide in the presence of catalytic amounts of ammonium molybdate, hydrogen peroxide in glacial acetic acid or an organic peracid (such as peracetic acid), chromium trioxide, ruthenium tetroxide, nitric acid, and N-chlorosuccinimide in methanol/water.

If free amino groups are present in the compounds of the formula (III) used as the starting material, these are in general provided with protective groups, such as benzyloxycarbonyl, tert.-butoxycarbonyl or β-dicarbonyl derivatives, by methods customary in peptide chemistry before the oxidation and these groups are split off again in the customary manner after the oxidation.

A suitable reactive derivative of the compound (IV) used as a starting compound in reaction variant (b) can be, for example, an imino derivative of the Schiff's base type, or an amine tautomer which is formed by reacting the compound (IV) with a carbonyl compound, and furthermore a silyl derivative, which is formed by reacting the compound (IV) with a silyl compound, such as bis-(trimethylsilyl)-acetamide or trimethylsilylacetamide, and furthermore a derivative which is formed by reacting the compound (IV) with phosphorus trichloride or phosgene.

A suitable salt of the compound (IV) can be an acid addition salt, for example an organic acid salt, such as an acetate, maleate, tartrate, benzenesulphonate or toluenesulphonate, or an inorganic acid salt, such as a hydrochloride, hydrobromide, sulphate or phosphate, a metal salt, such as a sodium, potassium, calcium or magnesium salt, an ammonium salt or an inorganic amine salt, such as a triethylamine or dicyclohexylamine salt.

The suitable reactive carboxylic acid derivative of the compound (V) can be an acid halide, an acid anhydride, an activated amide or an activated ester. Examples which may be mentioned of such derivatives of the compound of formula (V) are an acid chloride, acid azide, mixed acid anhydride with an acid such as a substituted phosphoric acid, for example a dialkylphosphoric acid, phenylphosphoric acid, diphenylphosphoric acid, dibenzylphosphoric acid or a halogenated phosphoric acid, a dialkylphosphorous acid, sulphurous acid, thiosulphuric acid, sulphuric acid, an alkylcarbonic acid, an aliphatic carboxylic acid, for example pivalic acid, pentanecarboxylic acid, isopentanecarboxylic acid, 2-ethylbutyric acid or trichloroacetic acid, or an aromatic carboxylic acid, for example benzoic acid, or a symmetric acid anhydride, an activated amide formed with imidazole, dimethylpyrazole, triazole or tetrazole or an activated ester, such as a cyanomethyl, methoxymethyl, dimethyliminomethyl, vinyl, propargyl, p-nitrophenyl, 2,4-dinitrophenyl, trichlorophenyl, pentachlorophenyl, mesylphenyl, phenylazophenyl, phenylthio, p-nitrophenylthio, p-cresylthio, carboxymethylthio, pyranyl, pyrridyl, piperidyl or 8-quinolylthio ester or an ester with N,N-dimethylhydroxylamine, 1-hydroxy-2-(1H)-pyridone, N-hydroxysuccinimide, N-hydroxyphthalimide or 1-hydroxy-6-chloro-1H-benzotriazole.

The salts of the compound (V) can be salts with an inorganic base, for example alkali metal salts, such as sodium salts or potassium salts, or alkaline earth metal salts, such as calcium salts or magnesium salts, a salt with an organic base, such as trimethylamine, triethylamine or pyridine, or a salt with an acid, such as hydrochloric acid or hydrobromic acid.

The reaction variant (b) is as a rule carried out in a conventional solvent, such as water, acetone, dioxane, acetonitrile, chloroform, methylene chloride, ethylene chloride, tetrahydrofuran, ethyl acetate, N,N-dimethylformamide or pyridine, or any other organic solvent which does not have an adverse effect on the reaction, in particular a polar solvent. Of these solvents, the hydrophilic solvents can be used as mixtures with water.

If the compound (V) is used in the reaction in the form or a free acid or in the form of its salt, the reaction is preferably carried out in the presence of a conventional condensing agent, such as N,N-dicyclohexylcarbodiimide, N-cyclohexyl-N'-morpholinoethylcarbodiimide, N-cyclohexyl-N'-(4-diethylaminocyclohexyl)-carbodiimide, N,N-diethylcarbodiimide, N,N-diisopropylcarbodiimide, N-ethyl-N'-(3-dimethylaminopropyl)-carbodiimide, N,N-carbonyl-bis-(2-methylimidazole), pentamethyleneketene-N-cyclohexylimide, diphenylketene-N-cyclohexylimide, ethoxyacetalene, ethylpolyphosphate, isopropylpolyphosphate, diethyl phosphorochloridite, phosphorus oxychloride, phosphorus trichloride, thionyl chloride, oxalyl chloride, tirphenylphosphine, N-ethyl-7-hydroxybenzisoxazolium fluoborate, N-ethyl-5-phenylisoxazolium 3'-sulphonate, 1-(p-chlorobenzenesulphonyloxy)-6-chloro-1H-benzotriazole, a so-called Vilsmeier reagent, such as (chloromethyl)dimethylammonium chloride (prepared by reacting dimethylformamide with thionyl chloride or phosgene) or a compound which is prepared by reacting dimethylformamide with phosphorus oxychloride.

The reaction variant (b) can also be carried out in the presence of an inorganic or organic base, for example an alkali metal hydroxide, an alkali metal bicarbonate, an alkali metal carbonate, an alkali metal acetate, a trialkylamine, pyridine, an N-alkylmorpholine, an N,N-dialkylbenzylamine or an N,N-dialkylaniline. If the base or the condensing agent is liquid, it can also be used as the solvent. The reaction temperature is not critical and the reaction is as a rule carried out with cooling or at room temperature.

If the compounds of the formula (IV) used as the starting material for reaction variant (b) contain free amino groups, these are in general first provided with protective groups, for example benzyloxycarbonyl or tert.-butoxycarbonyl, by a method customary in peptide chemistry. When the reaction has ended, these protective groups are split off again in the customary manner.

The 6-aminopenicillanic acid 1,1-dioxide used as the starting material can be prepared by a procedure in which 6-aminopenicillanic acid is first converted into 6-benzyloxycarbonylaminopenicillanic acid by reaction with carbobenzoxy chloride, the 6-benzyloxycarbonylaminopenicillanic acid is then oxidized with potassium permanganate, and the carbobenzoxy protective group is then split off hydrogenolytically in the presence of a palladium catalyst.

The compounds of the present invention display an antimicrobial activity, coupled with low toxicity. These properties enable then to be used as chemotherapeutic active compounds in medicine and as substances preserving inorganic and organic materials, especially organic materials of all kinds, for example polymers, lubricants, paints, fibers, leather, paper and timber, and foodstuffs and water.

Examples of micro-organisms against which the active compounds of the formula (I) display an action are: Micrococcaceae, such as Staphylococci, for example Staphyloccus aureus, Staphylococcus epidermis, Staphylococcus aerogenes and Gasskya tetragena; Lactobacteria ceae, such as Streptococci, for example *Streptococcus pyogenes,* and *Diplococcus pneumoniae; Neisseriaceae, such as Neisserae, for example Neisseia gonorrhoeae, Neisseria meningitidis, Neisseria catarrhalis* and *Neisseia flava;* and Bacillaceae, such as aerobic spore-forming Bacillaceae, for example *Bacilus anthracis, Bacillus subtilis* and *Bacillus cereus.*

The above list of pathogens is purely illustrative.

As stated above, the invention also relates to the use in human and veterinary medicine in combating bacterial diseases, of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampules or suppositories comprising a compound of the invention.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or submultiple (down to a fortieth) of a daily dose of the compound of the invention in association with a carrier and/or enclosed with an envelope. Whether the medicament contains a daily dose or, for example a half, a third or a quarter of a daily dose will depend on whether the medicament is to be administered once or, for example, twice, three times or four times a day respectively.

The pharmaceutical composition according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution, e.g. paraffin; (f) resorption accelerators, e.g. quaternary ammonium compounds; (g) surface active agents, e.g. cetyl alcohol, glycerol monostearate, (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular paft of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminum hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitan esters), microcrystalline cellulose, aluminum metahydroxide, bentonite, agar-agar and tragacanth or mixtures thereof.

All the pharmaceutical compositions according to the invention can also contain coloring agents and preservatives as well as perfumes and flavoring additions (e.g. peppermint oil and eucalyptus oil) and sweetening agents (e.g. saccharin).

The pharmaceutical compositions according to the invention generally contain from 0.1 to 99.5%, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example any of the following: tablets (including lozenges and granulates), pills, dragees, capsules, suppositories and ampules. Some of these forms may be made up for delayed release of the active ingredient. Some, such as capsules, include a protective envelope which renders the portions of the medicament physically discrete and coherent.

The preferred daily dose for administration of the medicaments of the invention is 500 mg to 10 g of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in human and non-human animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably orally or parenterally, especially intravenously or intramuscularly. Preferred pharmaceutical compositions and medicaments are thereof those adapted for administration such as oral or parenteral administration. Administration in the method of the invention is preferably oral or parenteral administration.

In general is has proved advantageous to administer amounts of from 5 mg to 1,000 mg/kg, preferably 10 mg to 200 mg/kg, of body weight per day, optionally in the form of several individual administrations, to achieve the effective results. An individual administration preferably contains the active compound or compounds according to the invention in amounts of 1 mg to about 250 mg/kg, in particular 10 mg to 100 mg/kg, of body weight. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, while in other cases the upper limit mentioned must be exceeded to achieve the desired results. Where larger amounts are administered it can be advisable to divide these into several individual administrations over the course of the day.

The new penicillanic acid 1,1-dioxide derivatives of the present invention are distinguished by an antibacterial action, which has been shown in vivo and in vitro, and by oral resorbability.

In order to broaden the spectrum of action and to achieve an increase in action, especially in the case of bacteria which form $\beta$-lactamase, the penicillanic acid 1,1-dioxide derivatives according to the invention can be combined with other antimicrobial active compounds, for example with $\beta$-lactam antibiotics, such as penicillins.

In order to broaden the spectrum of action and to achieve an increase in action, the penicillanic acid 1,1-dioxide derivatives according to the invention can also be combined with aminoglycoside antibiotics, such as gentamicin, kanamicin, sisomicin, amikacin or tobramicin.

The penicillanic acid 1,1-dioxide derivatives according to the invention inactivate, by inhibition or destruction, the bacterial enzymes which split the $\beta$-lactam ring ($\beta$-lactamases). The degradation of other penicillins, for example of amoxicillin, mezlocillin, ampicillin, azlocillin, penicillin G, carbenicillin and ticarcillin, is thereby prevented, and on the one hand their activity is thereby retained and on the other hand their spectrum of action is extended to bacteria which produce $\beta$-lactamase. This is demonstrated by the improvement in the minimum inhibitory concentrations (MIC) shown in Table 1.

TABLE 1

| Bacteria strain | MIC in E/ml | | |
|---|---|---|---|
| | A | B | C |
| E. coli T 7 | >256 | 64 + 64 | >256 |
| Klebsiella pneum. 1852 | 128 | 32 + 32 | >256 |
| Staphylococcus aeureus 1756 | 256 | 64 + 64 | >256 |

A = mezlocillin; B = mezlocillin + compound according to Example 1; C = compound according to Example 1.

Table 1 shows the improvement (equivalent to lowering) in the minimum inhibitory concentration (MIC) of mezlocillin in the case of strains which are otherwise resistant towards mezlocillin.

IN VITRO EXPERIMENTS

The compound of Example 1, which can be regarded as a typical representative of the compounds according to the invention, was diluted with Müller-Hinton nutrient broth, with the addition of 0.1% of glucose, to a content of 100 $\mu$g/ml. In each case, the nutrient solution contained $1 \times 10^5$ to $2 \times 10^5$ bacteria per ml. The small tubes containing this batch were each incubated for 24 hours and the degree of turbidity was then determined. Absence from turbidity indicates action. At a dosage of 1 μg/ml, the bacteria cultures inoculated with Staphylococcus aureus 133 were free from turbidity.

The following examples illustrate processes for the production of compounds of the present invention.

EXAMPLE 1

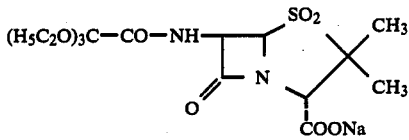

4 g of the sodium salt of 6-triethoxyacetamidopenicillanic acid were dissolved in 40 ml of water and the pH was adjusted to 7 to 7.5. A solution of 1.9 g of potassium permanaganate in 50 ml of water, and 0.66 ml of 85% strength phosphoric acid were then added dropwise at 0° C. in the course of about 20 minutes, during which the pH was kept at 6 to 7.5 by means of 10% strength phosphoric acid. The mixture was subsequently stirred for 10 minutes and any excess of potassium permanganate present was then removed by means of sodium bisulphite solution. The mixture was filtered over a filtration auxiliary, the material on the filter was rinsed with water, the combined aqueous filtrates were covered with a layer of ethyl acetate and the mixture was acidified to pH 2 at about 0° C. with dilute hydrochloric acid. The organic phase was separated off and the aqueous phase was extracted a further three times by shaking with ethyl acetate. The combined ethyl acetate extracts were extracted with water (the pH adjusted to 7) and the aqueous phase was then freeze-dried. Yield: 3.85 g NMR (CD₃OD; 60 MHz): 5.9 (d), 5.0 (d), 4.25 (s), 3.6 (q), 1.5 (d) and 1.2 (t) ppm. (δ).

The 6-triethoxyacetamidopencillanic acid used as the starting material was prepared by reacting at 0° C., the mixed anhydride of triethoxyacetic acid and pivalic acid (prepared by reacting 7.9 g of potassium triethoxyacetate, 70 ml of tetrahydrofuran, 4.23 ml of pivaloyl chloride at −10° C. for 20 hours) with 6-aminopenicillanic acid (6.5 g dissolved in 60 ml of water at pH 7.5 by means of triethylamine). Yield: 12.5 g (sodium salt).

The following substances could be prepared in the same manner:

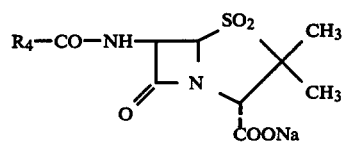

in which R₄ has the following meanings;

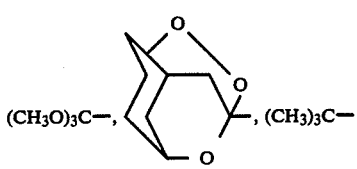

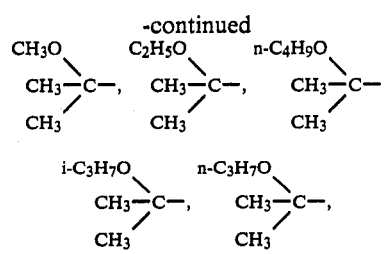

$(CH_3O-CH_2-CH_2-O)_3C-$ and $(n-C_3H_7O)_3C-$.

EXAMPLE 2

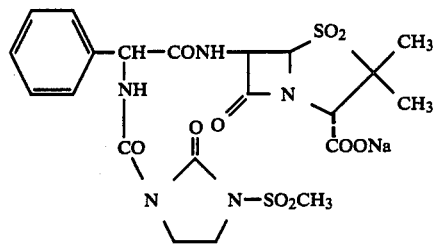

5.6 g of sodium D-α-[(2-oxo-3-methylsulphonylimidazolidine)-1-carboxamido]-benzylpenicillin in 50 ml of water were adjusted to pH 7 to 7.5 with 5% strength sodium hydroxide solution and the mixture was cooled to 0° C. A mixture of 1.57 g of potassium permanganate and 0.52 ml of 85% strength phosphoric acid in 40 ml of water was added in a manner such that the internal temperature was kept below 10° C. and the pH was kept between 6 and 7.5 (with sodium hydroxide solution or phosphoric acid). The mixture was subsequently stirred for 10 minutes and filtered over a filtration auxiliary, and the filtrate was cooled to 0° C. and, after 70 ml of ethyl acetate had been added, acidified to pH 2 with 6 N HCl. The ethyl acetate was separated off, the aqueous phase was extracted twice more with 50 ml of ethyl acetate each time and the combined organic phases were washed, dried over magnesium sulphate and evaporated. Yield: 5.4 g. According to the thin layer chromatogram, the product consisted of a 2:1 mixture of the desired product and the starting material. The material was thus reacted again with 0.7 g of potassium permanganate and 0.25 ml of phosphoric acid at pH 6 to 7.5 and the mixture was worked up, as indicated above. Yield of free acid isolated: 5.0 g (89% of theory). NMR (CD₃OD; 60 MHz): 2.4 to 2.7 (5H), 4.0 (1H), 4.35 (1H), 5.05 (1H), 5.55 (1H), 6.15 (4H), 6.75 (3H), 8.5 (3H) and 8.63 (3H) ppm. (τ scale).

EXAMPLE 3

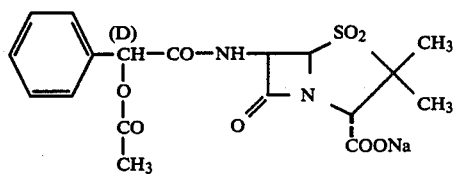

The compound was prepared from 4.2 g of sodium D-α-acetoxybenzylpenicillin as in Example 1. After acidification in ethyl acetate, the product was extracted, water was added, the pH was adjusted to 7 with 2 N sodium hydroxide solution and the aqueous phase was freeze-dried.

Yield: 4 g (92% of theory). NMR τ(D₂O; 60 MHz): 2.5 (5H), 3.9 (1H), 4.15 (1H), 4.85 (1H), 5.65 (1H), 7.85 (1H), 8.45 (3H) and 8.6 (3H) ppm.

EXAMPLE 4

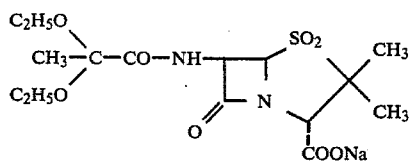

3.5 g of the sodium salt of 6-(2,2-diethoxy)pro-pionamidopencillanic acid were dissolved in 35 ml of water at pH 7 to 7.5, with 1 N sodium hydroxide solution. A solution of 1.8 g of potassium permanganate in 45 ml of water was then added dropwise at 0° C. and the pH was kept at 6 to 7.5 with 85% strength phosphoric acid. The mixture was stirred at 5° C. for 90 minutes and the excess of potassium permanganate was then removed by means of sodium bisulphite solution. The mixture was filtered, the material on the filter was washed with water, the combined filtrates were covered with a layer of ethyl acetate and the mixture was acidified to pH 2, while cooling with ice and stirring. The acid aqueous phase was then extracted twice more, at the same pH, with ethyl acetate. The combined organic phases were extracted by stirring with water, which was kept at pH 7 with 1 N sodium hydroxide solution. The neutral aqueous extract was then freeze-dried. Yield: 2.9 g. NMR (D₂O; 60 MHz): 6.0 (d), 5.3 (d), and 4.4 (s; 3-CH) ppm.

The sodium 6-(2,2-diethoxy)-propionamido)penicillianate used as the starting material was prepared from the mixed anhydride of 2,2-diethoxypropionic acid and pivalic acid (prepared from 7 g of potassium 2,2-diethoxypropionate and 4.3 ml of pivaloyl chloride in 70 ml of tetrahydrofuran at −10° C. in the course of about 24 hours) and 6-aminopencillanic acid (7.6 g, dissolved in 70 ml of water at pH 7.5 with the necessary amount of triethylamine) at 0° C. The mixture was worked up in the manner known for penicillins. Conversion into the sodium salt was effected by freeze-drying the neutral aqueous extract. Yield: 13.2 g. NMR (CD₃OD/D₂O; 60 MHz): 5.4 to 5.8 (dd; 5-CH and 6-CH), and 4.3 (s; 3-CH) ppm.

The following substances could be prepared in the same manner:

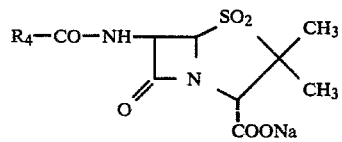

in which R₄ has the following meanings:

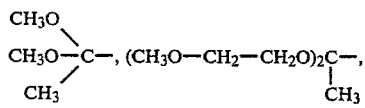

-continued

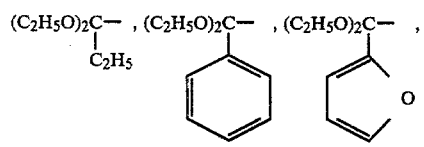

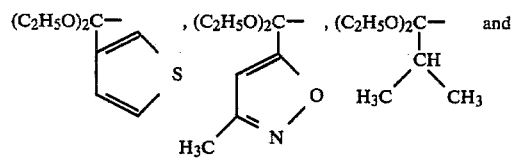

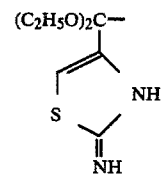

EXAMPLE 5

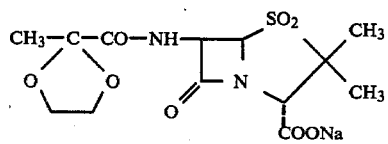

3.5 g of the sodium salt of 6-[2-(1,3-dioxolan-2-yl)-propionamido]-penicillanic acid were dissolved in 35 ml of water at pH 7 to 7.5 with 1 N sodium hydroxide solution. A solution of 1.95 g of potassium permanganate in 50 ml of water was then added dropwise at 0° C., and during this addition the pH was kept at 6 to 7.5 with 85% strength phosphoric acid. The mixture was stirred at 5° C. for 90 minutes. After removing the excess potassium permanganate with sodium bisulphite, the manganese dioxide formed was filtered off, the filtrate was extracted, at pH 2, with ethyl acetate and the desired substance was extracted from the organic phase at pH 7 with sodium hydroxide solution. This neutral aqueous extract was then freeze-dried. Yield: 2.6 g. NMR (D₂O; 60 MHz): 5.9 (d), 5.3 (d), 4.4 (s; 3-CH) and 3.9 to 4.3 (m; O-CH₂-CH₂-O) ppm. (δ scale).

The sodium 6-[2-(1,3-dioxolan-2-yl)-propionamido]-penicillanate used as the starting substance was prepared from the mixed anhydride of 2-(1,3-dioxolan-2-yl)-propionic acid and pivalic acid (prepared from 7.5 g of potassium 2-(1,3-dioxolan-2-yl)-propionate and 5.4 ml of pivaloyl chloride in 70 ml of tetrahydrofuran) and 9.5 g of 6-aminopenicillanic acid (dissolved, as the triethylamine salt, in 90 ml of water) at 0° C. The mixture was worked up in the manner known for penicillins. Conversions into the sodium salt was effected by freeze-drying the neutral aqueous extract. Yield: 6.5 g. NMR (CD₃OD/D₂O; 60 MHz): 5.6 (d), 5.4 (d), 4.2 (s; 3-CH), and 3.9 to 4.1 (m; O-CH₂-CH₂-O) ppm.

The following substances could be prepared in the same manner:

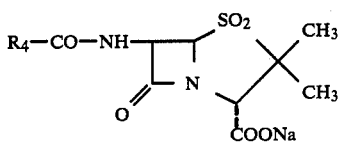

in which R₄ has the following meanings;

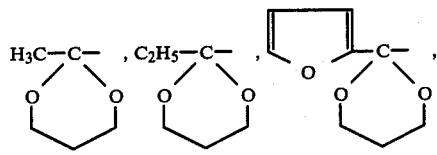

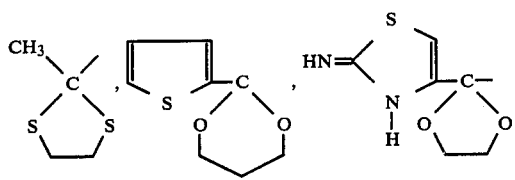

and

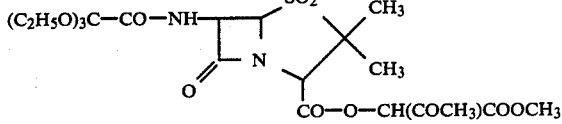

EXAMPLE 6

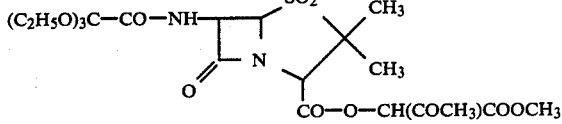

A mixture of 2 g of the substance from Example 1, 8 ml of N,N-dimethylacetamide and 0.61 g of 2-chloroacetoacetic acid methyl ester was stirred at 20° C. for 20 hours. The mixture was then poured into 100 ml of water and the resulting mixture was stirred for 2 hours. The product was decanted and dissolved in diethyl ether and this solution was washed 10 times with 50 ml of water each time. The organic phase was then dried, and evaporated in vacuo.

Yield: 0.3 g. NMR signals (60 MHz); CDCl₃, ): 5.7 (d, 1H), 4.9 (d, 1H), 4.7 (s.1H), 3.9 (s.3H), 3.8–3.4 (q, 6H), 2.4 (s.3H), 1.7 (s.3H), 1.6 (s.3H), and 1.4–1.1 (t, 9H), ppm.

EXAMPLE 7

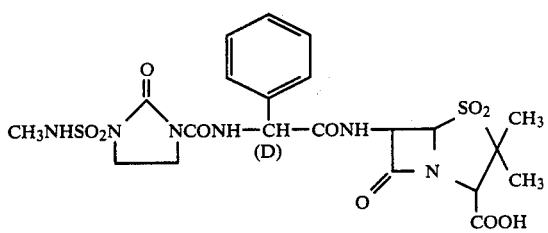

7.5 g of D-α-[(2-oxo-3-methylaminosulphonylimidazolidine)-1-carboxamido]-α-benzylpenicillin were reacted according to Example 2 to give the dioxide in 47% yield. IR bands at 1783, 1720, 1670, 1510, 1319, 1255, 1272 and 1115 cm⁻¹ (in Nujol).

EXAMPLE 8

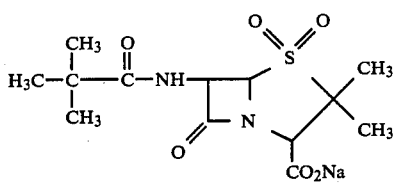

Starting from t-butyl-penicillin, t-butyl-penicillin 1,1-dioxide was obtained in a yield of 81% in the manner described in Example 1.

NMR (CD₃OD): 1.3 (s, 9H), 1.45 (s, 3 H), 1.55 (s, 3H), 4.2 (s, 1H), 4.95 (d, 1H), and 5.9 (d, 1H) ppm (δ scale).

EXAMPLE 9

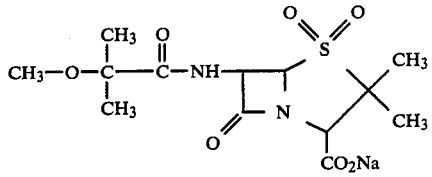

Starting from 1-methoxy-1-methylethylpenicillin, 1-methoxy-1-methylethylpenicillin 1,1-dioxide was obtained in a yield of 74% in the manner described in Example 1. NMR (CD₃OD): 1.35 (s, 6H), 1.4 (s, 3H), 1.5 (s, 3H), 3.2 (s, 3H), 4.2 (s, 1H), 4.9 (d, 1H), and 5.85 (d, 1H) ppm (δ scale).

EXAMPLE 10

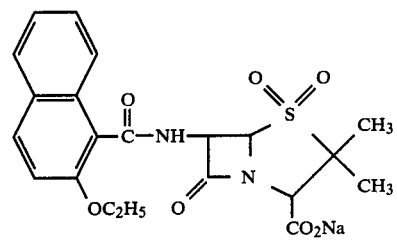

Starting from 2-ethoxy-1-naphthyl-penicillin. 2-ethoxy-1-naphthyl-penicillin 1,1-dioxide was obtained in a yield of 86% in the manner described in Example 1.
IR (KBr): 1790 (cm$^{-1}$)

The following compounds were obtained likewise:

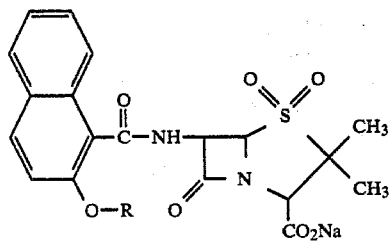

in which R has the following meanings: CH$_3$, i-C$_3$H$_7$, n-C$_3$H$_7$, n-C$_4$H$_9$.

Among the new penicillin 1,1-dioxide salts of the invention, those salts that are pharmaceutically acceptable are particularly important and are preferred.

The new free penicillin 1,1-dioxide of the general formula I and their salts can be interconverted in any suitable manner; methods for such interconversion are known in the art.

The present invention also comprises pharmaceutically acceptable bioprecursors of the active compounds of the present invention.

For the purposes of this specification the term "pharmaceutically acceptable bioprecursor" of an active compound of the invention means a compound having a structural formula different from the active compound but which nonetheless, upon administration to an animal or human being is converted in the patient's body to the active compound.

It will be appreciated that the instant specification and examples are set forth by way of illustration and not limitation, and that various modifications and changes may be made without departing from the spirit and scope of the present invention.

We claim:

1. A penicillin 1,1 dioxide of the formula

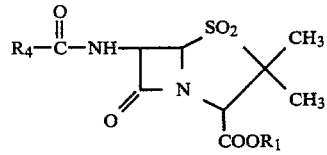

or a salt thereof, wherein

R$_1$ denotes a hydrogen atom or an ester-forming radical

R$_4$ denotes hydrogen; a naphthyl which is optionally substituted by R$_{16}$ wherein R$_{16}$ denotes halogen; amino; mono-lower alkylamino; di-lower alkylamino; pyrrolidyl; piperidyl; HCO—NH—; lower alkyl—CO—NH—; H—CO—N (lower alkyl); di-lower alkylamino- lower alkyl; lower alkyl—CO—N(lower alkyl)—; (lower alkyl)$_2$C=N—; lower alkyl—SO$_2$—NH—, lower alkyl—SO$_2$—N(lower alkyl)—; HO—SO$_2$—NH—; HO—SO$_2$—N(lower alkyl)—; amidino; (lower alkyl)$_2$—N—CH=N—;

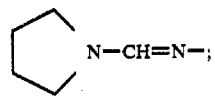

guanido; nitro; azido; hydroxyl; lower alkoxy; H—CO—O—; lower alkyl—CO—O—; lower alkyl—O—CO—O—; H$_2$N—CO—O—; lower alkyl—NH—CO—O—; (lower alkyl)$_2$N—CO—O—;

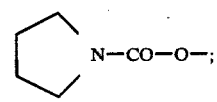

H$_2$N—SO$_2$—O—; lower alkyl—NH—SO$_2$—O—; (lower alkyl)$_2$N—SO$_2$—O—; HOOC—; H$_2$N—CO—; (lower alkyl)$_2$N—CO—; OHC—; HO—SO$_2$—O—; HS—; lower alkyl—S—;

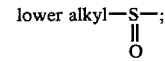

HO$_3$S—; lower alkyl—SO$_2$—; H$_2$N—SO$_2$—; lower alkyl—NH—SO$_2$—; (lower alkyl)$_2$N—SO$_2$—; or straight-chain or branched alkyl with 1 to 6 carbon atoms and phenyl or phenoxy;

or

wherein R$_5$ is H, aryl with 6–10 C-atoms, or heterocyclyl a hetero-paraffinic, hetero-aromatic or hetero-olefinic 5-membered to 7-membered ring with identical or different hetero-atoms selected from the group consisting of oxygen, sulphur and nitrogen and wherein X is oxygen or R$_{13}$—N R$_{13}$=hydroxy or alkoxy with 1–6 C-atoms optionally substituted by R$_{16}$;

or

R$_6$ and R$_7$ independently being C$_1$–C$_4$ alkyl optionally substituted with R$_{16}$ or C$_1$–C$_4$ alkoxy optionally substituted with R$_{16}$, or both together with the carbon atom to which they are bonded, denote dioxacyclopentane or dioxacyclohexane R$_8$ being optionally substituted C$_1$–C$_4$ alkyl or C$_1$–C$_4$ alkoxy or a phenyl, furyl, thienyl, methylisoxazolyl or aminothiazolyl.

2. A compound according to claim 1, in which said compound is

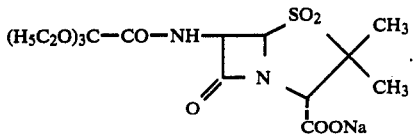

3. An antibacterial composition containing as an active ingredient an antibacterially effective amount of a compound or salt according to claim 1 in admixture with a diluent.

4. A composition according to claim 3, wherein the diluent comprises a β-lactam antibiotic which is unstable toward β-lactamase.

5. A composition according to claim 3, in unit dosage form in the form of a tablet, pill, dragee, capsule, ampule or suppository.

6. A method of combating bacteria which comprises administering to the bacteria, or a habitat thereof, an anti-bacterially effective amount of a compound or salt according to claim 1.

7. A method of combating bacterial infections in human and non-human animals which comprises administering to the animals an anti-bacterially effective amount of a compound or salt according to claim 1.

8. The method according to claim 6, in which said compound is

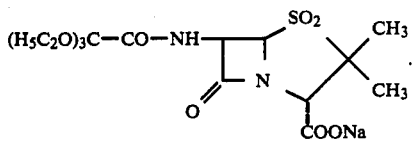

* * * * *